United States Patent
Doerr et al.

(10) Patent No.: US 9,364,681 B2
(45) Date of Patent: Jun. 14, 2016

(54) IMPLANTABLE HEART THERAPY DEVICE

(71) Applicant: BIOTRONIK SE & CO. KG, Berlin (DE)

(72) Inventors: Thomas Doerr, Berlin (DE); Andreas Kucher, Schwedt (DE)

(73) Assignee: BIOTRONIK SE & CO. KG, Berlin (DE)

( * ) Notice: Subject to any disclaimer, the term of this patent is extended or adjusted under 35 U.S.C. 154(b) by 41 days.

(21) Appl. No.: 14/324,025

(22) Filed: Jul. 3, 2014

(65) Prior Publication Data

US 2015/0025592 A1    Jan. 22, 2015

Related U.S. Application Data

(60) Provisional application No. 61/847,093, filed on Jul. 17, 2013, provisional application No. 61/865,625, filed on Aug. 14, 2013.

(51) Int. Cl.
| | |
|---|---|
| *A61N 1/39* | (2006.01) |
| *A61N 1/362* | (2006.01) |
| *A61N 1/365* | (2006.01) |
| *A61N 1/368* | (2006.01) |
| *A61N 1/37* | (2006.01) |

(52) U.S. Cl.
CPC ............ *A61N 1/3987* (2013.01); *A61N 1/3622* (2013.01); *A61N 1/3684* (2013.01); *A61N 1/36592* (2013.01); *A61N 1/37* (2013.01); *A61N 1/3962* (2013.01)

(58) Field of Classification Search
CPC .... A61N 1/362; A61N 1/3962; A61N 1/3622
USPC .................................................. 607/4, 5, 14
See application file for complete search history.

(56) References Cited

U.S. PATENT DOCUMENTS

| | | |
|---|---|---|
| 2007/0270911 A1 | 11/2007 | Doerr |
| 2008/0269817 A1 | 10/2008 | Veillette et al. |
| 2009/0125077 A1 | 5/2009 | Doerr et al. |
| 2009/0264947 A1 * | 10/2009 | Doerr .................. A61N 1/3622 607/4 |
| 2009/0306731 A1 * | 12/2009 | Doerr .................. A61N 1/3962 607/5 |
| 2011/0082512 A1 | 4/2011 | Doerr et al. |
| 2013/0030314 A1 | 1/2013 | Keel et al. |

OTHER PUBLICATIONS

European Search Report dated Aug. 29, 2014, 5 pages.
Barold, Serge, et al., "Dissimilar Ventricular Rhythms: Implications for ICD Therapy", Heart Rhythm: The Official Journal of the Heart Rhythm Society, XP009178789 Elsevier, USA (2013).

* cited by examiner

*Primary Examiner* — Catherine Voorhees
*Assistant Examiner* — Roland Dinga
(74) *Attorney, Agent, or Firm* — ARC IP Law, PC; Joseph J. Mayo

(57) ABSTRACT

An implantable heart therapy device connected to at least one right-ventricular electrode and one left-ventricular electrode that sense and stimulate the heart. The at least one right-ventricular and left-ventricular electrodes are each connected to a tachycardia identification unit, wherein the identification unit identifies ventricular tachycardias, and simultaneously evaluates the heart rate at the right-ventricular and at the left-ventricular electrodes. The implantable heart therapy device includes a right-ventricular stimulation unit that delivers antitachycardia stimulation to the right-ventricular electrode, a left-ventricular stimulation unit that delivers antitachycardia stimulation to the left-ventricular electrode, and a therapy control unit that assigns the stimulation location for the antitachycardia stimulation to the slower ventricle side if a dissimilar tachycardia is present.

9 Claims, 8 Drawing Sheets

IMPLANTABLE HEART THERAPY DEVICE

This application claims the benefit of U.S. Provisional Patent Application 61/847,093, filed on 17 Jul. 2013, and U.S. Provisional Patent Application 61/865,625, filed on 14 Aug. 2013, the specifications of which are hereby incorporated herein by reference.

BACKGROUND OF THE INVENTION

1. Field of the Invention

Embodiments of the invention generally relate to an implantable heart therapy device having a therapy control unit that includes a tachycardia identification unit. The heart therapy device also includes a right-ventricular stimulation unit and a left-ventricular stimulation unit, wherein both the right-ventricular stimulation unit and the left-ventricular stimulation unit are connected to the therapy control unit. The therapy control unit triggers antitachycardia stimulation (ATP).

2. Description of the Related Art

European Patent 1 857 140 to Doerr et al., entitled "Heart Stimulator", discloses a heart therapy device having a stimulation unit that is connected or can be connected to a stimulation electrode in order to stimulate a ventricle of a heart. The stimulation unit, of Doerr et al., may generate both stimulation pulses and defibrillation shocks, and may include at least one high-voltage capacitor, in which the electrical energy necessary for a defibrillation shock is stored.

Generally, heart therapy devices may include a detector that processes physiological signals received from the heart and, on the basis thereof, detects the presence of an acute ventricular tachycardia or fibrillation. Typically, heart therapy devices may also include a control unit connected to the detector and the stimulation unit, wherein the control unit is responsive to an output signal of the detector to control the stimulation unit to deliver a sequence of stimulation pulses or to deliver a defibrillation shock forming an antitachycardia therapy. The heart therapy device of Doerr et al. enables therapy delivery to a right ventricle of the heart.

Generally, heart therapy devices may be referred to as implantable cardioverter-defibrillators (ICD). Typically, heart therapy devices referred to herein are primarily implantable heart therapy devices that are able to treat tachycardia of the heart.

Generally, the term "tachycardias" includes both tachycardias represented by a stable heartbeat with pathologically high frequency, and also fibrillations. Therapies delivered by a heart stimulator, generally, include an antitachycardia stimulation or a defibrillation shock.

A defibrillation shock is typically an electrical pulse delivered to the heart and has sufficiently high voltage and energy to fully excite a heart chamber affected by fibrillation to therefore make the heart chamber refractory. Therefore, re-entrant excitation pulses, typical for fibrillations, are interrupted. In the case of tachycardia wherein a ventricle is affected, the tachycardia is often also referred to as ventricular tachycardia and is abbreviated by VT (in contrast to ventricular fibrillation VF). Generally, successful therapy is often possible using antitachycardia stimulation (antitachyarrhythmia pacing: ATP). Generally, with antitachycardia stimulation, the heart stimulator outputs a sequence of stimulation pulses, of which the energy is significantly lower than the energy of a defibrillation shock and which are not painful. Typically, with antitachycardia stimulation, such stimulation pulses of comparatively low energy are delivered with a frequency that is greater than the frequency of the determined tachycardia. Generally, tachycardia may be stopped in this way without a patient suffering from pain or without the energy demand being particularly high.

Typical therapy devices generally deliver stimulation pulses to one or both ventricles of a heart, to the left ventricle (LV) and/or to the right ventricle (RV). Such therapy devices are generally referred to as biventricular therapy devices.

Generally, previous ICD systems available on the market may operate exclusively with a right-ventricular VT/VF identification channel for the tachycardia identification and for the corresponding therapy selection. Typically, the stimulation location of the ATP may be programmed statically (RV, LV, BiV).

Generally, ICD systems may also provide, in the VF zone, an ATP therapy attempt, which is delivered immediately before or with the onset of charging, but only when the right-ventricular rhythm meets a frequency and/or stability criterion at the same time; such as an ATP one shot.

Typically, purely right-ventricular sensing used with current ICD systems may have the disadvantage that, in the event of dissimilar ventricular tachyarrhythmia, an incorrect therapy may be selected. If, for example, the rhythm in the right ventricle is already in a VF zone and is unstable, but the left ventricle is still stable, generally, the selection of a defibrillation shock is preferred over an ATP, although clinical observations show that an ATP delivery, for example in the left ventricle, may have a higher therapy success rate.

Generally, a further disadvantage of current systems includes the exclusive use of right-ventricular sensing for synchronization of a left-ventricular ATP. Typically, the exclusive use of right-ventricular sensing may be the reason why no clinical studies are known that demonstrate an advantage of left-ventricular ATP.

Generally, one-time ATP attempts in the VF zone do not take into account the left-ventricular rhythm and also do not take into account potential rhythm regularization during the charging time, and therefore potentially effective ATP attempts are not delivered.

BRIEF SUMMARY OF THE INVENTION

At least one embodiment of the invention includes an implantable therapy device that enables high therapy efficiency of antitachycardia stimulation (ATP).

One or more embodiments of the invention include an implantable heart therapy device having a therapy control unit, which includes a tachycardia identification unit connected, at least indirectly, to at least one right-ventricular sensing electrode and at least one left-ventricular sensing electrode. In at least one embodiment of the invention, the at least one right-ventricular sensing electrode and the at least one left-ventricular sensing electrode may feed at least one signal from the heart's right ventricle and at least one signal from the heart's left ventricle, respectively, to the tachycardia identification unit. In one or more embodiments, the signals represent a course over time of electrical potentials in the heart. During operation, in one or more embodiments, the signals representing a course over time of electric potentials in the heart or signals derived therefrom are fed to the tachycardia identification unit. By way of at least one embodiment, the tachycardia identification unit may evaluate the signals fed thereto and/or the course over time thereof, and may generate a tachyarrhythmia signal if the (fed) signal meets predefined criteria. In at least one embodiment, the tachycardia identification unit may simultaneously evaluate the heart rate at the at least one right-ventricular sensing electrode and at the at least one left-ventricular sensing electrode to identify ventricular tachycardia.

According to one or more embodiments, the implantable heart therapy device may include a right-ventricular stimulation unit and a left-ventricular stimulation unit connected to the therapy control unit. The right-ventricular stimulation unit and the left-ventricular stimulation unit, in at least one embodiment, may, in combination with the therapy control unit, generate stimulation pulses for one or more of a right-ventricular and a left-ventricular antitachycardia stimulation therapy (ATP). In at least one embodiment, the right-ventricular stimulation unit and the left-ventricular stimulation unit may deliver the stimulation pulses via the at least one right-ventricular stimulation electrode or the left-ventricular stimulation electrode connected thereto, respectively.

In one or more embodiments, the tachycardia identification unit may detect and determine a dissimilar tachycardia that is greater than the heart rates sensed via the right-ventricular sensing electrode and via the left-ventricular sensing electrode. In at least one embodiment, the therapy control unit may control a delivery of the stimulation pulses for one or more of the right-ventricular and the left ventricular antitachycardia stimulation via the at least one right-ventricular or the at least one left-ventricular stimulation electrode, such that the stimulation pulses for antitachycardia stimulation are delivered via the stimulation electrode which is assigned to the same ventricle as the at least one right-ventricular sensing electrode or the at least one left-ventricular sensing electrode via which, in the event of the dissimilar tachycardia, at least one signal representing the lower heart rate is established or detected. In at least one embodiment, the control of the delivery of the stimulation pulses may be based on a frequency criterion for a selection of a therapy channel, wherein the therapy channel denotes a stimulation unit, of one or more of the right-ventricular stimulation unit and the left-ventricular stimulation unit, assigned to a respective ventricle.

At least one embodiment of the invention uses biventricular sensing to optimize the therapy efficiency of the antitachycardia stimulation (ATP) to automatically determine the (ATP) stimulation location (RV, LV) in patients with dissimilar ventricular tachycardias. The heart therapy device, according to one or more embodiments of the invention, enable a considerable increase in the efficiency of the antitachycardia stimulation and thus simultaneously reduce the need for defibrillation therapies, for example shock reduction.

The heart therapy device, according to at least one embodiment of the invention, may include an implantable defibrillator connected to at least one right-ventricular electrode and to at least one left-ventricular electrode that sense and stimulate the heart. In one or more embodiments, each of the at least one right-ventricular electrode and the at least one left-ventricular electrode are connected to the tachycardia identification unit. In at least one embodiment, the tachycardia identification unit may identify ventricular tachycardias, and may evaluate the heart rate at the at least one right-ventricular and at the at least one left-ventricular electrode simultaneously. The heart therapy device, such as the implantable defibrillator, in at least one embodiment, includes a right-ventricular stimulation unit that delivers antitachycardia stimulation to the right-ventricular electrode, a left-ventricular stimulation unit that delivers antitachycardia stimulation to the left-ventricular electrode. In one or more embodiments, the heart therapy device may include an evaluation control unit that may be part of the therapy control unit wherein the evaluation control unit may determine the stimulation location for the antitachycardia stimulation on the slower ventricle side when dissimilar tachycardia is present.

By one or more embodiments of the invention, the heart therapy device enables the therapy efficiency of the ATP to rise significantly and thus reduces the number of necessary shock deliveries. At least one embodiment of the invention includes a 3-chamber ICD, wherein a considerable proportion of episodes with dissimilar ventricular tachycardias may exist, and the progressions of a rhythm of quick tachycardias may also experience regularization over time.

In one or more embodiments, independent of the selection of the ventricle for an ATP that presents the lower heart rate, the therapy device may include the evaluation control unit that may be part of the therapy control unit, such that, during charging of one or more shock capacitors for defibrillation therapy, the evaluation control unit may continuously scan one or both ventricle channels after regularization of the rhythm and, in the case of regularization (for example using a stability criterion), may deliver an ATP attempt during the charging of the one or more shock capacitors in the respective ventricle channel.

In at least one embodiment, the right-ventricular stimulation unit and the left-ventricular stimulation unit may include the one or more shock capacitors that store energy for a defibrillation shock, or are connected thereto. In one or more embodiments, the therapy control unit, during the charging of the one or more shock capacitors for defibrillation therapy, may analyze the signals representing the course over time of the electric potentials in the heart, or the signals derived therefrom, with regard to a regularization of the rhythm represented by the signals. In at least one embodiment, where appropriate, the therapy control unit may detect regularization during the charging of the one or more shock capacitors and therefrom may trigger an antitachycardia stimulation via the stimulation electrode assigned to the same ventricle as the sensing electrode via which the signals representing a regularized rhythm are recorded.

In one or more embodiments, a defibrillation shock may be avoided at the last moment and, where appropriate, complete charging of the one or more shock capacitors may also be avoided, such that energy is saved and the patient is saved from a painful defibrillation shock.

In at least one embodiment, the therapy control unit may carry out a stability evaluation of the rhythm represented by the signals representing the course over time of the electric potentials in the heart or the signals derived therefrom, and may trigger an antitachycardia stimulation via the stimulation electrode that is assigned to the same ventricle as the sensing electrode via which the signals representing a stable or more stable rhythm are recorded (for example using the stability criterion for the selection of the therapy channel).

In one or more embodiments, the selection of the therapy channel (such as the right-ventricular stimulation unit and/or the left-ventricular stimulation unit via which an ATP is delivered) may be dependent on one or more of the heart rate detected via a respective sensing channel (such as the at least one right-ventricular or the at least one left-ventricular sensing electrode assigned to the respective ventricle), and on the stability of the rhythm represented by the detected signals. In at least one embodiment, the therapy control unit may trigger an antitachycardia stimulation via the at least one right-ventricular or the at least one left-ventricular stimulation electrode that is assigned to the same ventricle as the at least one right-ventricular or the at least one left-ventricular sensing electrode, via which signals representing a stable or more stable rhythm are recorded, even independently of whether signals representing a slower rhythm are recorded via the respective sensing electrode.

According to one or more embodiments, the therapy control unit may use the frequency criterion preferentially or exclusively when selecting the therapy channel, or may use the stability criterion preferentially or exclusively. In at least one embodiment, the therapy control unit may apply the frequency criterion when selecting the therapy channel and may additionally apply the stability criterion. In one or more embodiments, the therapy control unit, in the event of a dissimilar tachycardia, may initially determine the sensing electrode via which the lower heart rate is detected, and may then check whether the signals detected via the respective sensing electrode, of the at least one right-ventricular sensing electrode and the at least one left-ventricular sensing electrode, represent a sufficiently stable rhythm. In at least one embodiment, the sufficiently stable rhythm may be a more stable or similarly stable rhythm compared to the signals recorded via the other sensing electrode of the at least one right-ventricular sensing electrode and the at least one left-ventricular sensing electrode.

By way of one or more embodiments of the invention, the therapy control unit may, in the event of a dissimilar tachycardia, trigger one or more antitachycardia stimulations and may suppress a delivery of a defibrillation shock provided the signals detected via one or more of the at least one right-ventricular sensing electrode and the at least one left-ventricular sensing electrode represent a stable rhythm. In at least one embodiment, one or more ATP attempts may be provided instead of shock therapy, when one of the ventricle sides, of the right ventricle and the left ventricle, has a stable rhythm.

In at least one embodiment, the therapy control unit may determine whether the signals from one or more of the at least one right-ventricular sensing electrode and the at least one left-ventricular sensing electrode represent a rhythm above a programmable limit value. If so, in one or more embodiments of the invention, the therapy control unit may trigger only a single individual antitachycardia stimulation and may trigger simultaneously or immediately thereafter a charging process by a shock capacitor, of the one or more shock capacitors, for a defibrillation shock. In one or more embodiments, if one of the ventricle sides is already located in the VF zone or above a programmable limit value, only an individual ATP attempt is delivered, and the charging process for defibrillation is started simultaneously or immediately thereafter.

In one or more embodiments, the therapy control unit may check a success of the triggered antitachycardia stimulation during the charging of the one or more shock capacitors and, when the therapy control unit detects success of the triggered antitachycardia stimulation, the therapy control unit may suppress a delivery of the defibrillation shock. In one or more embodiments, the success of the ATP attempt may be evaluated during the charging of the one or more shock capacitors or before shock delivery, such as an ATP one shot.

In at least one embodiment, the implantable heart therapy device may include an implantable biventricular cardioverter-defibrillator (ICD), wherein the ICD may include a metal housing and a terminal housing. In one or more embodiments, the metal housing may include the therapy control unit, the left-ventricular stimulation unit, the right-ventricular stimulation unit, and one or more electrical components including the one or more shock capacitors. In at least one embodiment, the terminal housing may be connected to electrode lines, wherein the electrode lines may include the at least one right-ventricular sensing electrode, the left-ventricular sensing electrode, the right-ventricular stimulation electrode and the left-ventricular stimulation electrode.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
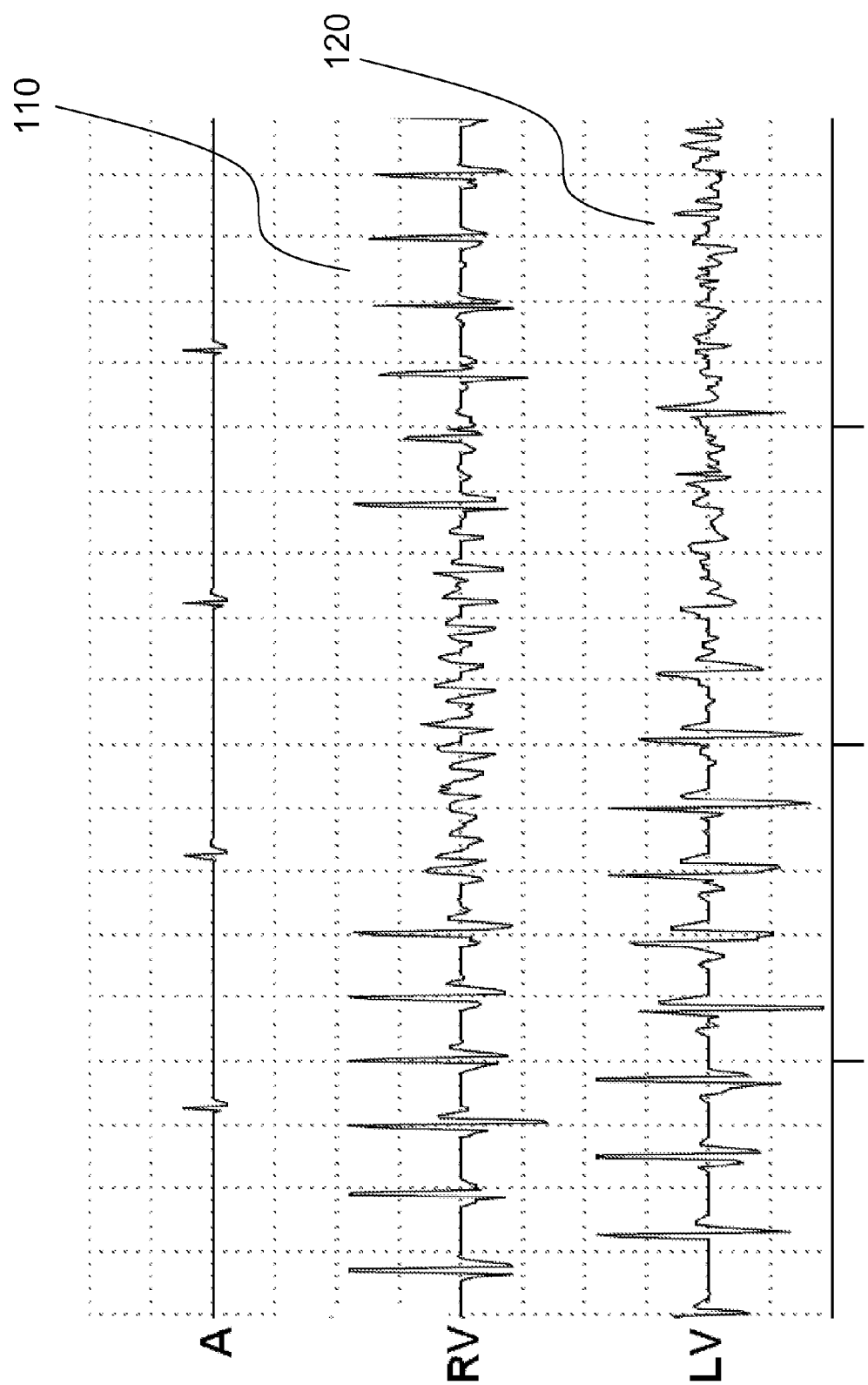
FIG. 1 shows an example of dissimilar ventricular tachyarrhythmia.

FIG. 1 shows an example of a dissimilar ventricular tachyarrhythmia. As shown in FIG. 1, the rhythm changes in the right ventricle (RV) from a stable VT over a short phase of VF to slower VT 110, and at the same time the rhythm in the LV channel changes at a later moment in time from a stable VT to a lasting VF 120, which is not sensed with a purely right-ventricular detection and may lead to an incorrect choice of therapy.

Figure 2:
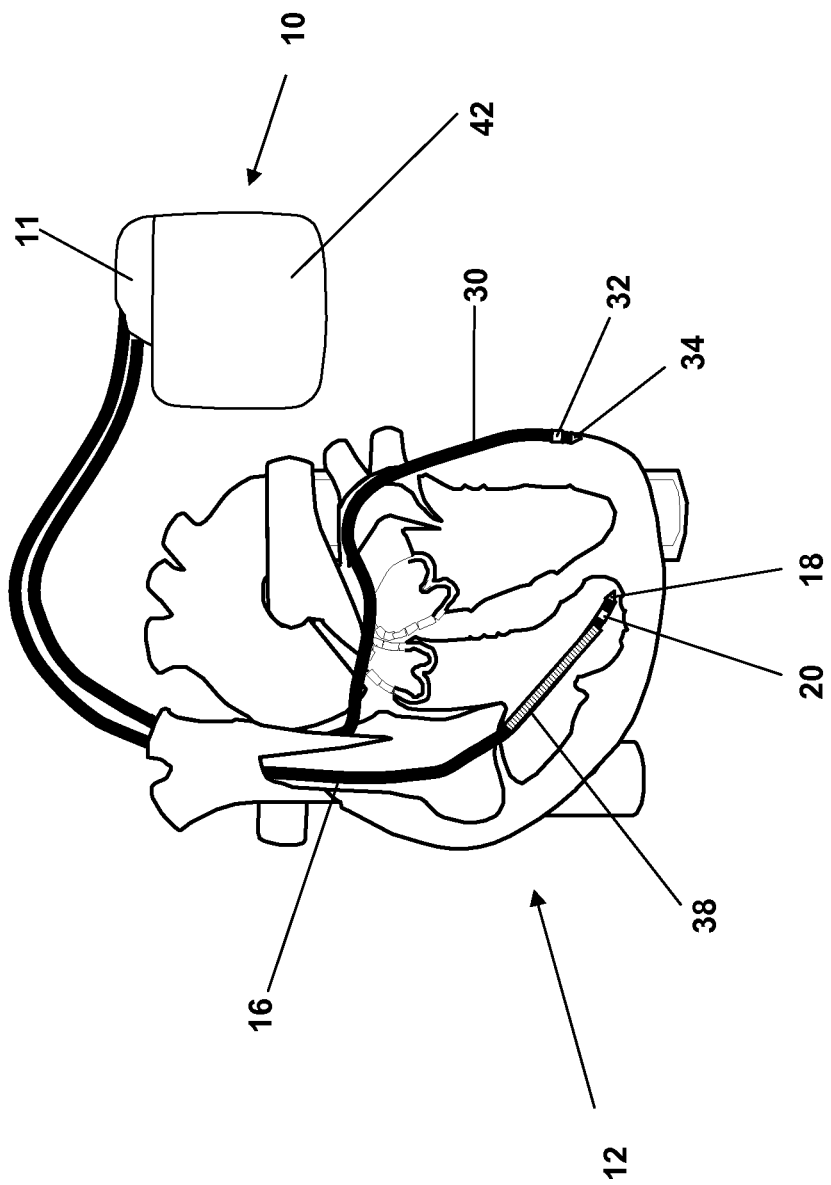
FIG. 2 shows an implantable heart therapy device, such as an implantable heart stimulator, as a biventricular cardiac pacemaker with a right-ventricular defibrillation shock coil, according to at least one embodiment of the invention.

FIG. 2 shows a biventricular cardiac pacemaker-defibrillator (ICD or CRT-D), having a right-ventricular defibrillation shock coil, as an implantable heart therapy device (or heart stimulator) 10, according to at least one embodiment of the invention. In one or more embodiments, the implantable heart therapy device 10 includes electrode lines 16 and 30 connected thereto. The implantable heart therapy device 10, in at least one embodiment, is connected via the electrode lines 16 and 30 to stimulation electrodes 18 and 20, and to sensing electrode 32 and 34, in the right and left ventricle of a heart respectively. In one or more embodiments, the heart therapy device may deliver stimulation pulses to the heart and record electric potentials from the heart.

In at least one embodiment, the heart therapy device 10 may include a housing 42, such as a metal housing, with a terminal block or header 11 for the electrode lines 16 and 30.

The electrode lines 16 and 30, in at least one embodiment, are electrically connected via plug connections to contact sockets in the header (terminal housing) 11 of the heart stimulator 10. In one or more embodiments, the electrode lines 16 and 30 may be connected to one or more electronic components inside a hermetically tight metal housing 42 of the heart stimulator 10. The one or more electronic components, according to at least one embodiment, schematically illustrated in FIG. 3, may determine the operating principles of the heart stimulator 10.

In one or more embodiments, the electrode line 16 is a right-ventricular electrode line and has at its distal end a right-ventricular tip electrode pole RV Tip 18, and in a direct or indirect vicinity thereof, a right-ventricular ring electrode pole RV Ring 20. In at least one embodiment, both electrode poles may be arranged in the apex of the right ventricle of the heart and may be used for right-ventricular sensing and stimulation, and thus form a sensing and stimulation electrode. In one or more embodiments, the sensing may be carried out via the ring electrode pole RV Ring 20 and tip electrode pole RV Tip 18 as a bipolar electrode pole, wherein stimulation pulses may be delivered via the tip electrode pole RV Tip 18 alone. In one or more embodiments, the electrode line 16 may include a right-ventricular shock coil RV Shock 38 as a large-area electrode pole that delivers defibrillation shocks. In at least one embodiment, the housing 42 may be a counter electrode.

In at least one embodiment, the heart therapy device 10 may include a left-ventricular electrode line 30 implanted via a coronary sinus, and may include a bipolar electrode pole that senses and stimulates the left ventricle.

In one or more embodiments, the left-ventricular electrode line 30 may include a bipolar stimulation and sensing electrode at its distal end. In at least one embodiment, the bipolar stimulation and sensing electrode may include a distal tip electrode pole LV Tip 34, and in the direct or indirect vicinity thereof, a left-ventricular ring electrode pole LV Ring 32. In one or more embodiments, the two electrode poles LV Tip 34 and LV Ring 32 may be used for right-ventricular sensing and stimulation, and may include a sensing and stimulation electrode. In at least one embodiment, the sensing may be carried out via the ring electrode pole LV Ring 32 and the tip electrode pole LV Tip 34 as a bipolar electrode pole, wherein left-ventricular stimulation pulses may be delivered via the tip electrode pole LV Tip 34 alone. In one or more embodiments, the left-ventricular electrode line 30 may be guided from the right atrium 26 of the heart 12 via the coronary sinus into a lateral vein branching therefrom, also referred to as the coronary sinus electrode line or CS electrode line.

Figure 3:
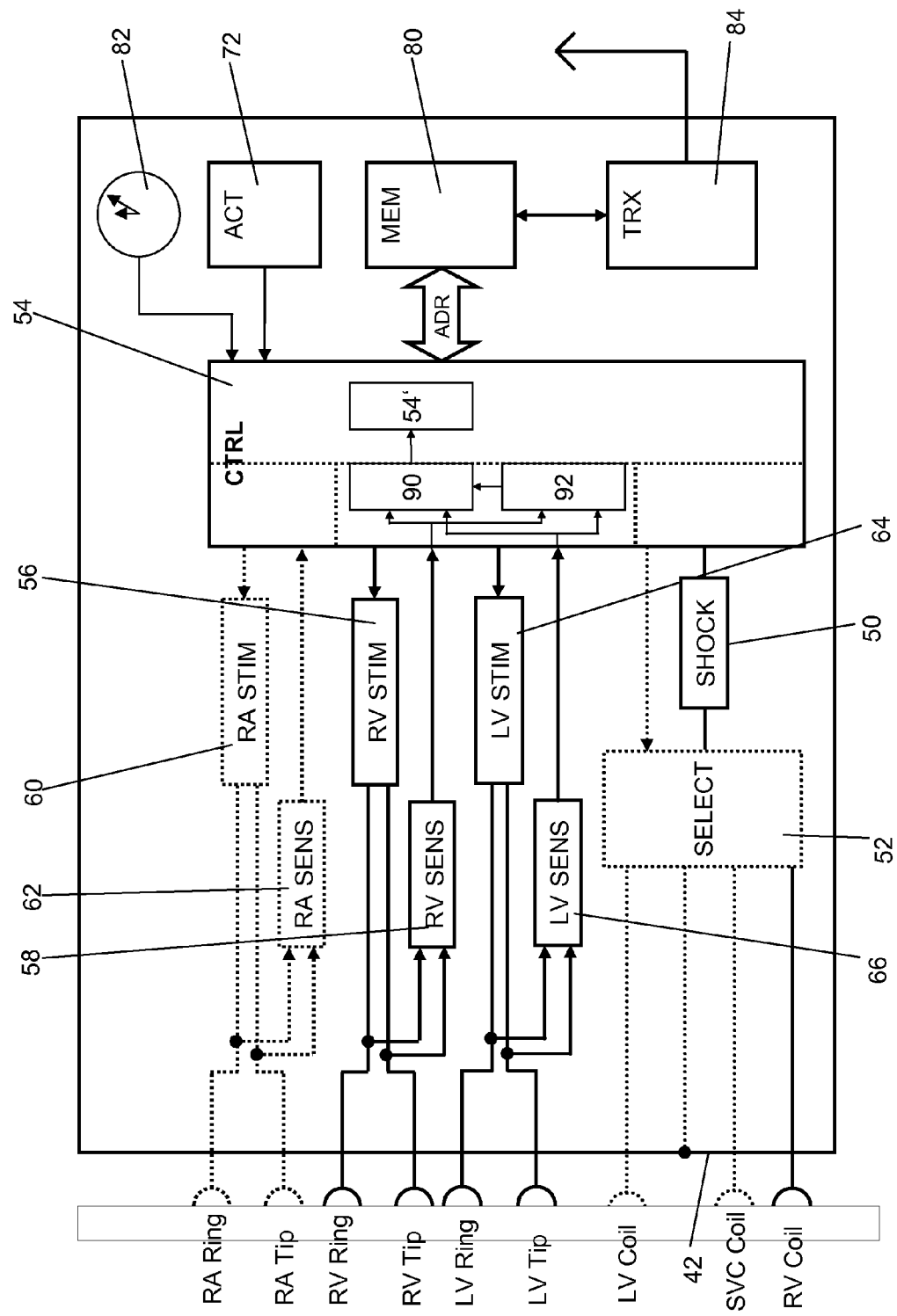
FIG. 3 shows a simplified block diagram with components of the implantable heart stimulator of FIG. 2, according to at least one embodiment of the invention.

FIG. 3 shows components, such as key functional units, of the heart stimulator 10. As shown in FIG. 3, additional components are illustrated via dashed lines, as may be provided in at least one embodiment of the invention.

By way of one or more embodiments, as shown on the left-hand side, electrical terminals for the various electrode poles 18, 20, 32, 34 and 38 are illustrated. The shock electrode (shock coil) 38, in at least one embodiment, is connected to a shock pulse generator 50. In one or more embodiments, the shock pulse generator 50 may be connected to a control unit 54, which controls the shock pulse generator 50, as required, to generate and deliver a cardioversion or defibrillation shock. In at least one embodiment, the control unit 54 acts as a therapy device control unit 54'. The therapy device control 54' may be connected, for example, to the shock pulse generator 50, to a right-ventricular stimulation unit 56, and to a left-ventricular stimulation unit 64.

The control unit 54, in at least one embodiment, may include a tachycardia identification unit 90 and a dislocation identification unit 92.

By way of one or more embodiments, the terminal for the right-ventricular tip electrode pole RV Tip, and the terminal for the right-ventricular ring electrode pole RV Ring, are each connected to both the right-ventricular stimulation unit 56 and to a right-ventricular sensing unit 58. Both the right-ventricular stimulation unit 56 and the right-ventricular sensing unit 58, in one or more embodiments, are each connected to the control unit 54.

According to at least one embodiment, the right-ventricular stimulation unit 56, following a control signal of the control unit 54, may generate a right-ventricular stimulation pulse and may deliver the right-ventricular stimulation pulse via the terminals for the right-ventricular ring electrode pole and the right-ventricular tip electrode pole. In one or more embodiments, the housing 42 of the heart stimulator 10 may form a neutral electrode, and the right-ventricular stimulation unit 56 may be connected to the terminal for the right-ventricular tip electrode pole RV Tip and to the housing 42 as another electrode to deliver a stimulation pulse. In at least one embodiment, the right-ventricular stimulation pulse differs from a defibrillation shock in that the stimulation pulse has a much lower pulse intensity, such that, by contrast to a defibrillation shock, it does not excite the entire heart tissue (myocardium) of a heart chamber in one attempt, but only excites the heart muscle cells in the direct vicinity of the right-ventricular tip electrode pole 18. In one or more embodiments, the excitation then propagates further as a result of natural conduction over the entire ventricle and thus ensures a stimulated contraction of the ventricle.

In at least one embodiment, the right-ventricular sensing unit 58 may first amplify, using an input amplifier, and then filter electric potentials applied across the terminal for the right-ventricular ring electrode pole RV Ring and the right-ventricular tip electrode pole RV Tip. By way of one or more embodiments, the right-ventricular sensing unit 58 may evaluate the course of the electric signals applied across its inputs in such a way that the right-ventricular sensing unit 58 automatically detects a natural (intrinsic) beat, such an as automatic contraction of the right ventricle. In at least one embodiment, the evaluation may be achieved, for example, by comparing the course of the signal applied across the inputs of the right-ventricular sensing unit 58 to a threshold value. In one or more embodiments, the largest amplitude of the signal is in the form of an R-spike, which is characteristic for a natural contraction of the right ventricle and which may be detected by comparison with a threshold value. In at least one embodiment, the right-ventricular sensing unit 58, therefrom, may output a corresponding output signal (for example a marker signal), indicating a natural contraction of the right ventricle, to the control unit 54, the tachycardia identification unit 90 and to the dislocation identification unit 92 thereof.

In one or more embodiments, the terminal for the left-ventricular tip electrode pole LV Tip and the terminal for the left-ventricular ring electrode pole LV Ring are also connected to the left-ventricular stimulation unit 64 and a left-ventricular sensing unit 66. In at least one embodiment, the left-ventricular stimulation unit 64 and the left-ventricular sensing unit 66 may be connected to the control unit 54. In one or more embodiments, both the left-ventricular stimulation unit 64 and the left-ventricular sensing unit 66 may function similarly to the stimulation units 56 and 60 and sensing units 58 and 62 as described above.

In at least one embodiment, the heart stimulator 10 may include an activity sensor 72 connected to the control unit 54 and generally includes timer 82. The activity sensor 72, in one or more embodiments, may detect a signal, for example a motion signal, dependent on the physical activity of a patient and may output a corresponding signal, indicating the physical activity of the patient, to the control unit 54. As such, in at least one embodiment, the control unit 54 may adapt the timing of the stimulation pulse to the demand of the patient (hemodynamic demand).

According to at least one embodiment, the heart stimulator 10 may include a memory unit 80, connected to the control unit 54, that stores signals generated or evaluated by the control unit 54. In one or more embodiments, the memory unit 80 may store control programs for the control unit 54 in modifiable form. In at least one embodiment, the control unit 54 may be connected to a timer 82.

By way of one or more embodiments, the heart stimulator 10 may include at least one bidirectional telemetry interface 84 to transfer stored data from the implant 10 to an external device 100 and, vice versa, to also receive program settings and therapy commands from the external device 100.

Figure 4:
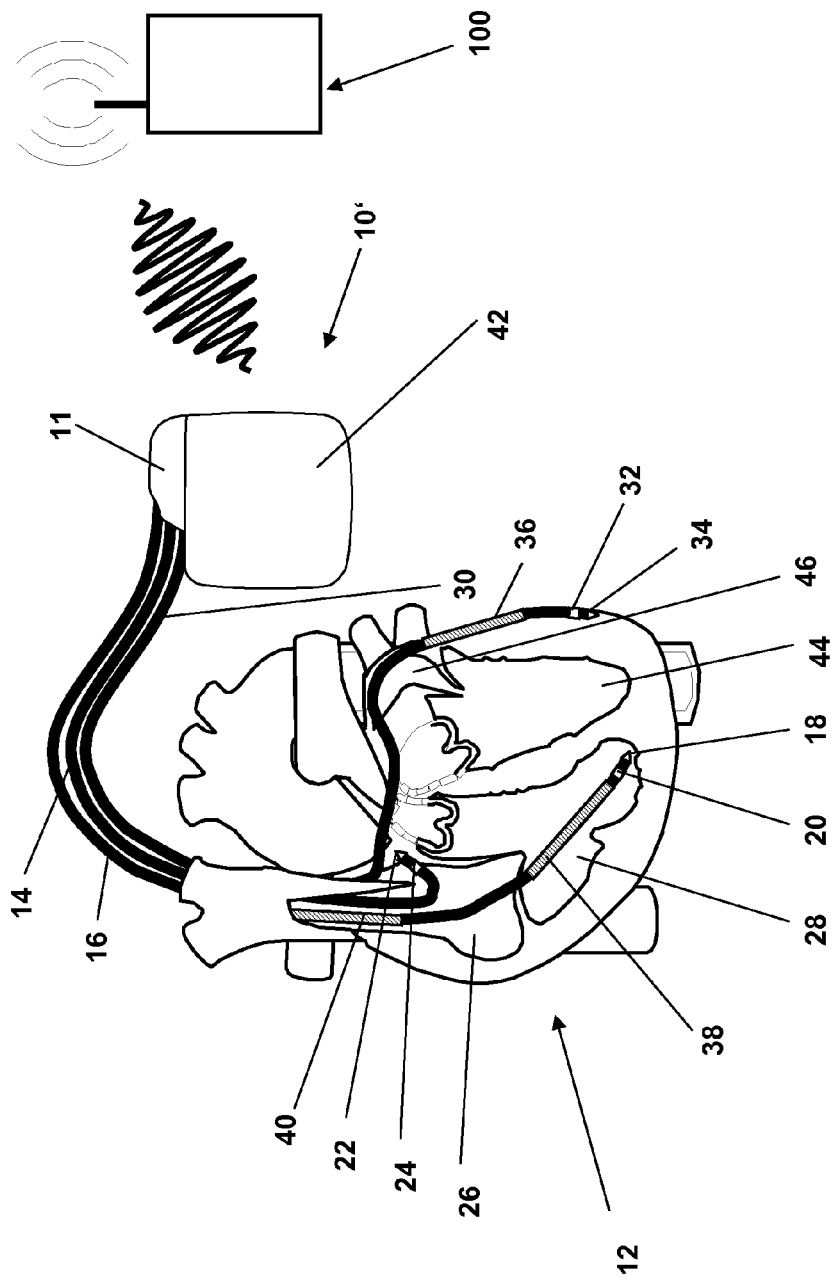
FIG. 4 shows a biventricular three-chamber cardiac pacemaker and an implantable cardioverter-defibrillator (ICD) as the implantable heart stimulator, according to at least one embodiment of the invention.

FIG. 4 shows a biventricular three-chamber cardiac pacemaker and implantable cardioverter-defibrillator (ICD) as an implantable cardiac stimulator. As shown in FIG. 4, the implantable cardiac stimulator 10', in at least one embodiment, is connected via its terminal block 11 (header) to one or more of a right-ventricular electrode line 16, a left-ventricular electrode line 30, and a right-atrial electrode line 14.

In one or more embodiments, at least one of the electrode lines 16, 30 and 14, may be implanted permanently in the heart 12. In at least one embodiment, the right-ventricular electrode line 16 has at the distal end a bipolar stimulation and sensing electrode with a tip electrode pole RV Tip 18 and a ring electrode pole RV Ring 20. According to at least one embodiment, the electrode line 16 may include a distal shock coil RV Coil 38 and additionally a proximal shock coil SVC Coil 40. The distal shock coil RV Coil 38, in at least one embodiment, may be arranged such that it is located in the right ventricle 28. The proximal shock coil SVC Coil 40, in at least one embodiment, may be located in the upper part of the right atrium 26 or in the superior vena cava (precava).

By way of one or more embodiments, the electrode line 14 is an atrial electrode line and may include at the distal end a bipolar stimulation and sensing electrode, formed by a tip electrode pole RA Tip 22 and a ring electrode pole RA Ring 24. The electrode line 14 is implanted in the right atrium 26.

As shown in FIG. 4, according to one or more embodiments, the left-ventricular electrode line 30 may include a left-ventricular shock coil 36 that delivers defibrillation shocks to the left ventricle. In at least one embodiment, the shock coil 36 may reach out from the left ventricle 44 as far as the left atrium 46. In at least one embodiment, the implantable cardiac stimulator 10' may include a second electrode, to deliver a shock, as the electrically active housing 42 of the implant 10'.

As shown from FIG. 3, in at least one embodiment of the invention, according to the components illustrated in a dotted manner, the terminal for the right-atrial tip electrode pole and the terminal for the right-atrial ring electrode pole may be connected both to a right-atrial stimulation unit 60 and to a right-atrial sensing unit 62, which are each in turn connected to the control unit 54. In one or more embodiments, the right-atrial stimulation unit 60 may generate stimulation pulses, of which the intensity is sufficient to excite the right-atrial myocardium. In at least one embodiment, the right-atrial stimulation pulses may have pulse intensity that is different from the right-ventricular stimulation pulses. The right-atrial sensing unit 62, in at least one embodiment, may detect a P-wave from the course of the differential signal applied across the inputs thereof, wherein the P-wave represents a natural (intrinsic) contraction of the right atrium. If the right-atrial sensing unit 62 detects a corresponding P-wave, in at least one embodiment of the invention, it generates an output signal and forwards the output signal to the control unit 54, wherein the output signal represents a natural contraction of the right atrium.

As also shown in FIG. 3, according to the components illustrated in a dotted manner, the left-ventricular shock coil 36, as illustrated in FIG. 4, may be connected to the shock pulse generator 50 via a terminal LV-COIL and an electrode selection unit 52. Using the electrode selection unit 52, in one or more embodiments, the control unit 54 may select two or more electrodes (including the conductive housing 42) via which a shock is delivered.

According to the heart therapy devices illustrated in FIGS. 2 to 4, according to at least one embodiment of the invention, the tachycardic ventricular dysrhythmias may be classified by the right-ventricular 16 and/or the left-ventricular electrode line 30, primarily via the sensed heartbeats, wherein the frequency and frequency stability of both sides of the ventricle may be evaluated during therapy selection. If the frequencies of both ventricles differ significantly, in one or more embodiments, the slower rhythm is thus evaluated in terms of frequency and optionally stability. In at least one embodiment, an ATP is always delivered to the slower ventricle side, only if the ventricle side has a frequency below a programmable frequency limit, or if a stability is detected on the respective ventricle side.

Figure 5:
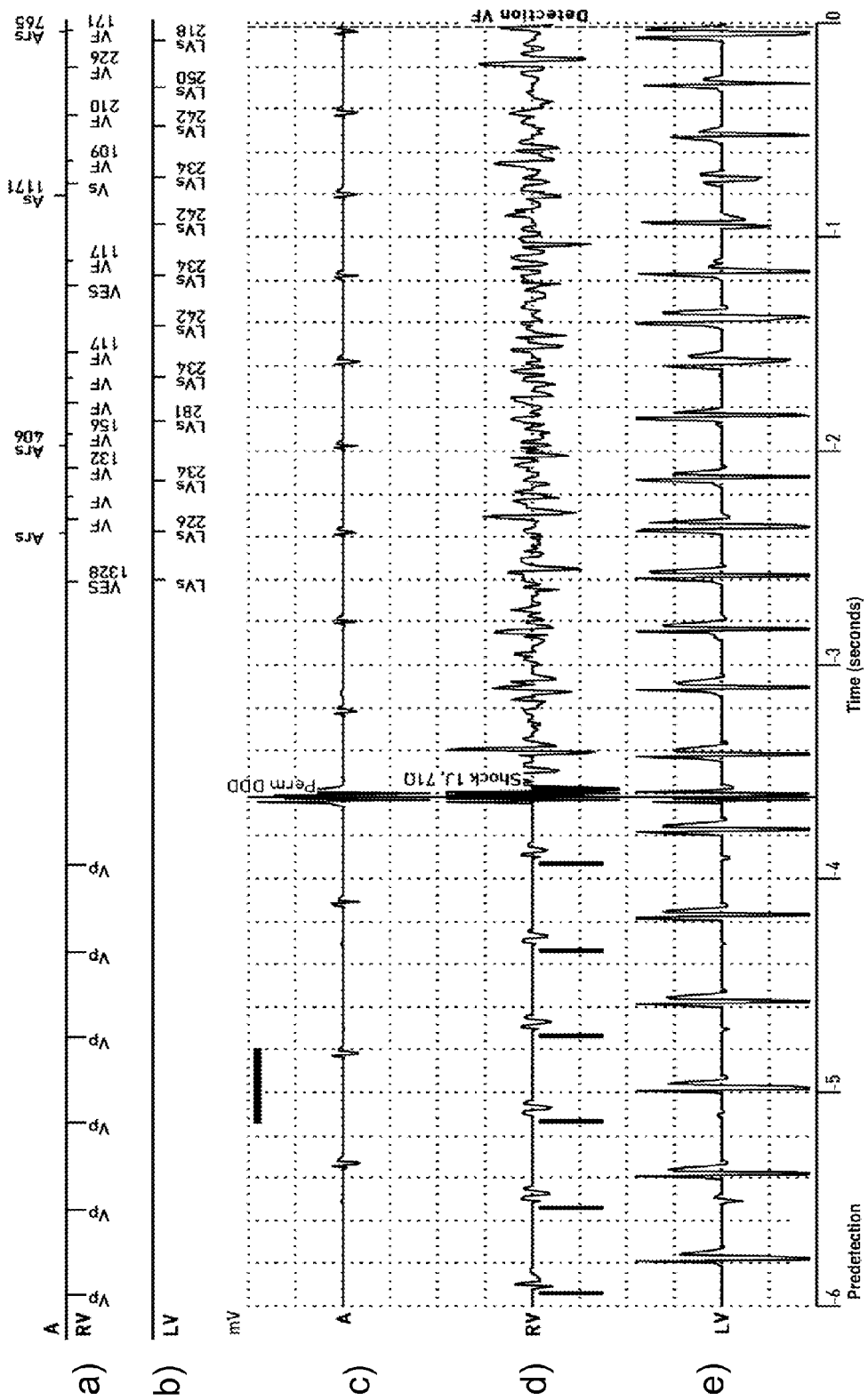
FIG. 5 shows an example of an induced dissimilar ventricular fibrillation and corresponding marker signals generated by the implantable heart therapy device, according to at least one embodiment of the invention.

FIG. 5 shows an example of an induced dissimilar ventricular tachycardia. As shown in FIG. 5, an unstable and very quick rhythm corresponding to a ventricular fibrillation is shown in the right-ventricular IEGM (RV), wherein a tachycardia with comparatively regular cycle length is shown in the left ventricle (LV).

In at least one embodiment, a dissimilar tachycardia may be classified by conventional ICD systems as ventricular fibrillation (VF; see "RV" line) and may always initiate defibrillation shock therapy.

According to one or more embodiments, a dysrhythmia may be treated successfully and painlessly using antitachycardia stimulation, if the ATP is applied to the slower, stable ventricle side. In at least one embodiment, an electrophysiological explanatory model may be based on a myocardial conduction and refractory period structure, for example in the left ventricle, wherein the right-ventricular structure may already demonstrate disassociated conduction and refractory period conditions. In one or more embodiments, as shown in FIG. 5, if the left-hand VT is successfully terminated by an ATP, the dysrhythmia may also terminate on the right-hand side with a high level of probability.

Figure 6:
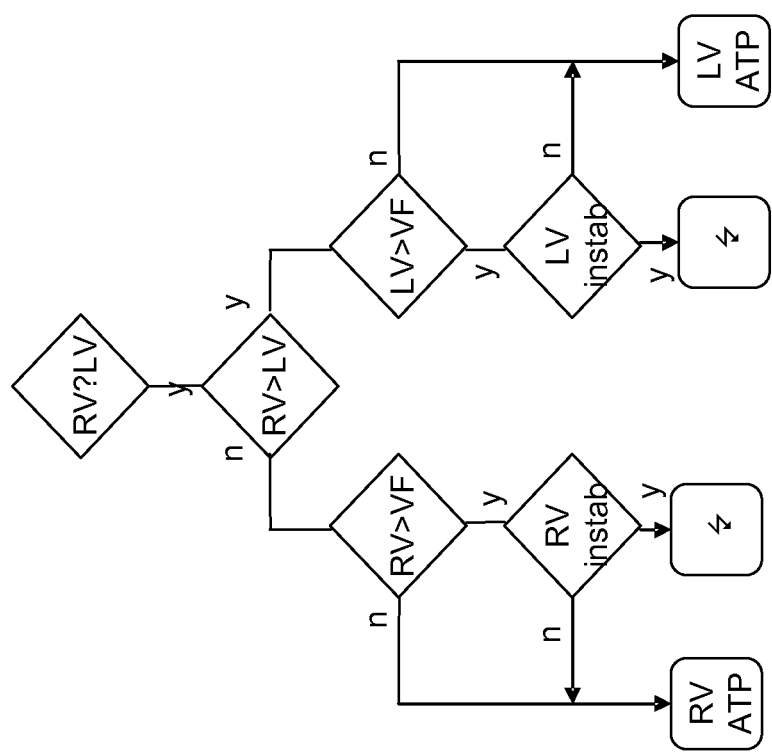
FIG. 6 shows a flow chart for therapy management in the event of dissimilar ventricular tachycardias according to at least one embodiment of the invention.

FIG. 6 shows a flow chart for therapy management in the event of dissimilar ventricular tachycardias, according to at least one embodiment of the invention.

In one or more embodiments, when a tachycardia is identified, the therapy control unit may first check for a dissimilarity (RV≠LV). If the rhythm is dissimilar, in at least one embodiment, then the therapy control unit may check which ventricle frequency, of the left ventricle and the right ventricle, is slower (RV>LV). In one or more embodiments, for the slower side, the therapy control unit may check whether the frequency already lies within the VF-zone requiring a shock (RV/LV>VF). If the frequency does not already lie in the VF-zone requiring a shock, by way of at least one embodiment, an ATP is delivered to the respective ventricle side. In at least one embodiment, if the rhythm on the slower ventricle side is also already within the VF-zone, a shock (↯) may then be immediately delivered if the rhythm is unstable (RV/LV unstab.), otherwise an ATP attempt may be delivered on the respective side. As such, in one or more embodiments, the therapy control unit may start the charging process for a shock either thereafter, or during the ATP delivery (such as ATP one shot).

Figure 7:
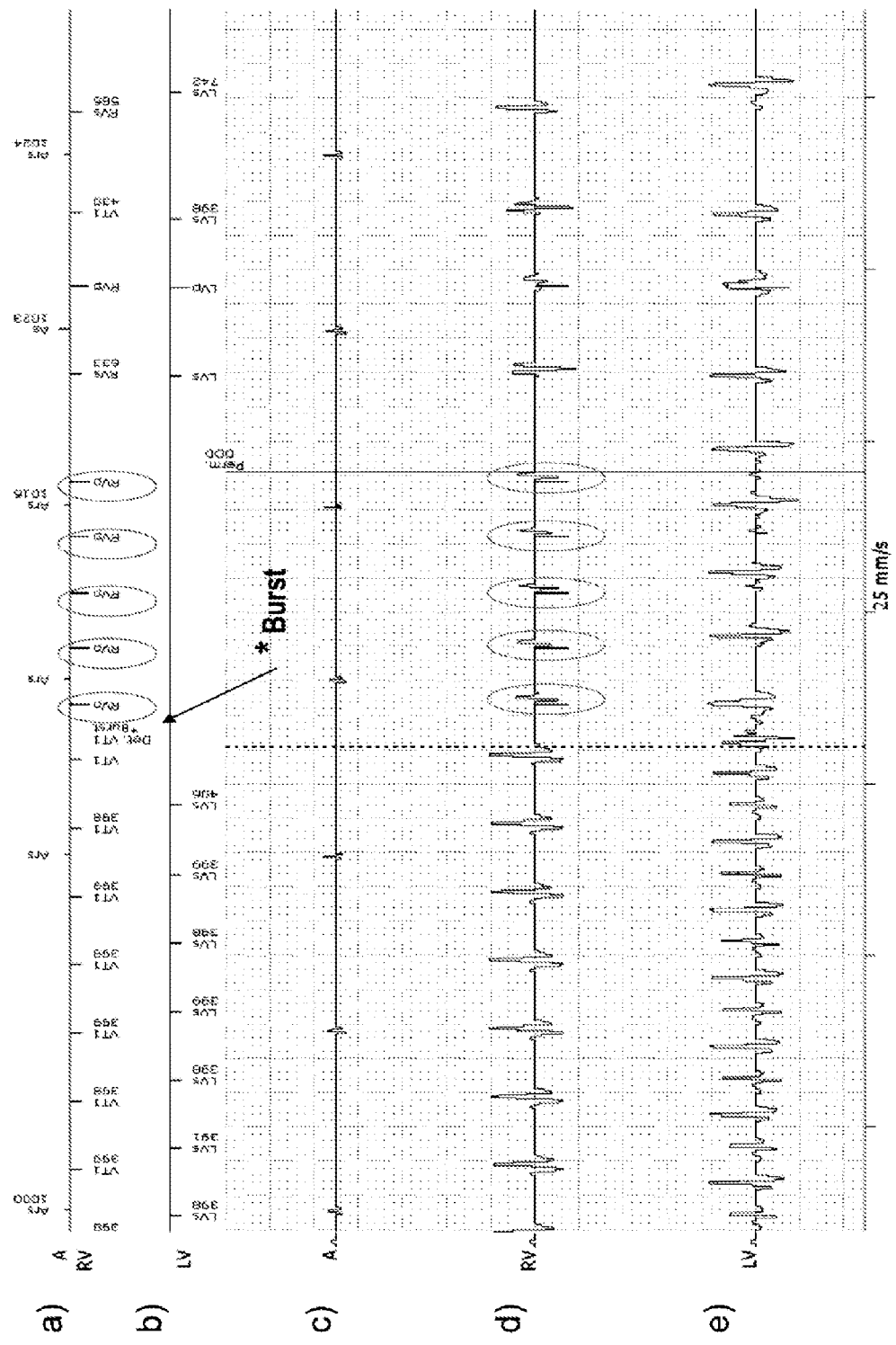
FIG. 7 shows an example of successful termination of dissimilar ventricular tachycardia, according to at least one embodiment of the invention.

FIG. 7 shows an example of successful termination of a dissimilar VT. As shown in FIG. 7, the frequency of the left-ventricular tachycardia may be twice as high as that of the right-ventricular VT, may fall within the VF-zone, and may be treated by shock therapy. According to at least one embodiment of the invention, an ATP (*Burst), delivered to the slower ventricle side (for example shown as the RV in FIG. 7), may successfully terminate the ventricular tachycardia, and therefore delivery of a shock is not needed.

Figure 8:
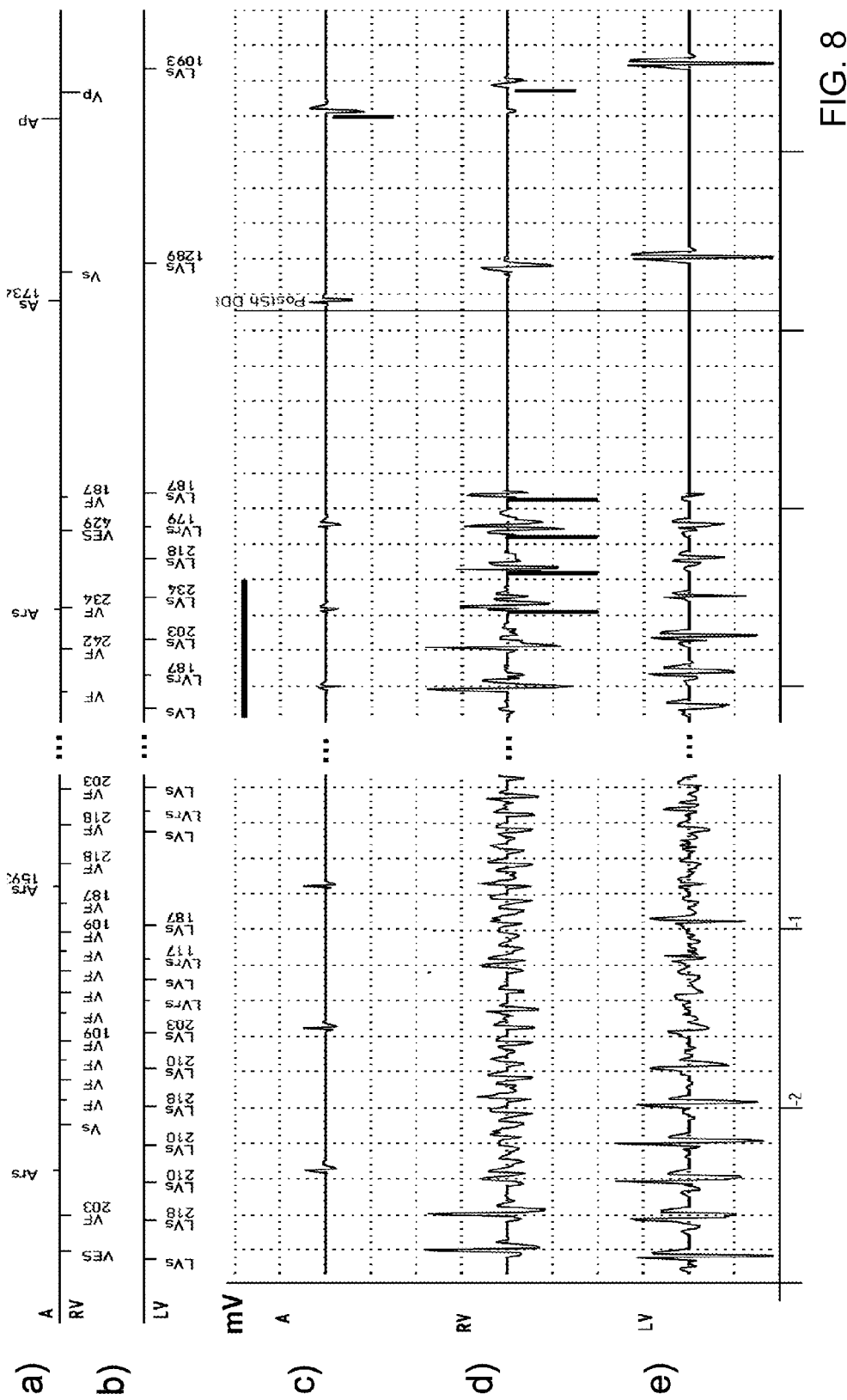
FIG. 8 shows an example of an ATP in the event of identified regularization of a VF, according to at least one embodiment of the invention.

FIG. 8 shows an example of an ATP in the event of identified regularization of a VF, according to at least one embodiment of the invention. As shown in FIG. 8, according to operating principles of the heart therapy device 10 and 10', the tachycardia identification unit 90 may continuously scan one or both ventricle channels after regularization of the rhythm during the charging of the one or more shock capacitors for defibrillation therapy. In one or more embodiments, the control unit 54, in the event of regularization (for example stability criterion), may trigger an ATP attempt during the charging of the one or more shock capacitors in the respective ventricle channel. FIG. 8 shows an irregular ventricular fibrillation, wherein according to at least one embodiment, after detection, may lead to charging of the one or more shock capacitors. In one or more embodiments, while the one or more shock capacitors are being charged, the rhythm in both ventricles, the left ventricle and the right ventricle, are checked for regularization, and, in the event of identified regularization, an ATP attempt may be delivered in the ventricle channel first classified as being regular (shown as the RV in FIG. 8). As shown in FIG. 8, according to at least one embodiment, the ATP is successful and shock delivery is therefore inhibited.

In one or more embodiments, a stability criterion, optionally with a programmable upper frequency limit, may be used as a criterion for regularization.

In at least one embodiment, using the stability criterion may reduce unnecessary shock deliveries, even in a single-chamber system.

One or more embodiments of the invention enable optimization of the therapy efficiency of antitachycardia stimulation, such as in the case of dissimilar and quick ventricular dysrhythmias, and thus serve to reduce the unnecessary shock deliveries in ICD therapy.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. An implantable biventricular cardiac therapy device (10) comprising:
   a therapy device control unit (54), wherein said therapy device control unit comprises
   a tachycardia detection unit (90) connected to at least one right-ventricular sensing electrode (18, 20) and at least one left-ventricular sensing electrode (32, 34),
      wherein said at least one right-ventricular sensing electrode and said at least one left-ventricular sensing electrode are configured to feed at least one signal from a left ventricle of a heart and a right ventricle of the heart, respectively, to the tachycardia detection unit (90),
      wherein said signals represent a course over time of electrical potentials in the heart,
      wherein the tachycardia detection unit (90) is configured to evaluate the signals fed thereto and the course over time thereof,
         generate a tachyarrhythmia signal when the signals meet predetermined criteria, and,
         evaluate a heart rate at the at least one right-ventricular sensing electrode and at the at least one left-ventricular sensing electrode simultaneously in order to detect ventricular tachycardias; and,
   a right-ventricular stimulation unit (56) and a left-ventricular stimulation unit (64) connected to the therapy device control unit (54),
      wherein the right-ventricular stimulation unit (56), the left-ventricular stimulation unit (64) and the therapy device control unit (54) are configured to
         generate stimulation pulses for one or more of a right-ventricular and a left-ventricular anti-tachycardiac therapy (ATP), and
         deliver the stimulation pulses via the at least one right-ventricular or said at least one left-ventricular stimulation electrode, respectively;
   wherein the tachycardia detection unit (90) is further configured to detect a dissimilar tachycardia, and
      determine which of the signals representing a course over time of electrical potentials in the heart represent a higher heart rate; and,
   wherein the therapy device control unit (54) is further configured to control a delivery of said stimulation pulses for one or more of said right-ventricular and said left-ventricular anti-tachycardiac stimulation via the at least one right-ventricular stimulation electrode and the at least one left-ventricular stimulation electrode, such that the stimulation pulses for the one or more of said right-ventricular and said left ventricular anti-tachycardiac stimulation are delivered via the at least one right-ventricular stimulation electrode or the at least one left-ventricular stimulation electrode that is assigned to a same ventricle as the at least one right-ventricular sensing electrode or the at least one left-ventricular sensing electrode via which, when the dissimilar tachycardia is detected, at least one signal representing a respectively lower heart is detected via the at least one right-ventricular sensing electrode or the at least one left-ventricular sensing electrode of said same ventricle.

2. The implantable biventricular cardiac therapy device (10) according to claim 1, wherein the right-ventricular stimulation unit (56) and the left-ventricular stimulation unit (64) comprise one or more shock capacitors configured to store energy for a defibrillation shock, and
   wherein the therapy device control unit (54) is further configured, during charging of the one or more shock capacitors for a defibrillation therapy, to
      analyze the signals representing the course over time of the electrical potentials in the heart using a regularization of a heart rhythm represented by the signals, detect a regularization during the charging of the one or more shock capacitors and, trigger one or more of the right-ventricular and the left-ventricular anti-tachycardiac stimulation via the at least one right-ventricular stimulation electrode or the at least one left-ventricular stimulation electrode that is assigned to the same ventricle as the at least one right-ventricular sensing electrode or the at least one left-ventricular sensing electrode, via which the signals representing a regularized rhythm are recorded.

3. The implantable biventricular cardiac therapy device (10) according to claim 1, wherein the therapy device control unit (54) is further configured to carry out a stability evaluation of the heart rhythm represented by the signals representing the course over time of the electrical potentials in the heart, and trigger one or more of and right-ventricular and the left-ventricular anti-tachycardiac stimulation via the at least one right-ventricular stimulation electrode or the left-ventricular stimulation electrode that is assigned to the same ventricle as the at least one right-ventricular sensing electrode or the at least one left-ventricular sensing electrode, via which signals representing a stable or more stable rhythm are recorded.

4. The implantable biventricular cardiac therapy device (10) according to claim 1, wherein the dissimilar tachycardia is detected, the therapy device control unit (54) is further configured to first determine via which sensing electrode of said least one right-ventricular sensing electrode or said at least one left-ventricular sensing electrode the at least one signal representing the respectively lower heart rate is detected, then check whether the at least one signal representing the lower heart rate detected via said at least one right-ventricular sensing electrode or said at least one left-ventricular sensing electrode of said same ventricle represents a sufficiently stable rhythm, wherein the sufficiently stable rhythm is a rhythm that is more stable than or as stable as the signals of the respective other sensing electrode of said at least one right-ventricular sensing electrode or said at least one left-ventricular sensing electrode, and, trigger a delivery of the stimulation pulses for one or more of the right-ventricular and the left-ventricular anti-tachycardiac stimulation via the at least one right-ventricular stimulation electrode or the at least one left-ventricular stimulation electrode that is assigned to the same ventricle as the at least one right-ventricular sensing electrode or the at least one left-ventricular sensing electrode which, wherein when the dissimilar tachycardia is detected, the at least one signal representing a respectively lower heart rate is detected via the at least one right-ventricular sensing electrode or the at least one left-ventricular sensing electrode of said same ventricle, provided the at least one represents a sufficiently stable rhythm.

5. The implantable biventricular cardiac therapy device (10) according to claim 1, wherein the therapy device control unit (54) is further configured to trigger one or more of said right-ventricular and said left-ventricular anti-tachycardiac stimulation and to suppress a delivery of a defibrillation shock, provided the signals detected via at least one of the sensing electrodes represent a stable rhythm.

6. The implantable biventricular cardiac therapy device (10) according to claim 1, wherein the therapy device control unit (54) is further configured to determine whether the signals from one or more of the at least one right-ventricular sensing electrode and the at leas one left-ventricular sensing electrode represent a rhythm above a programmable limit value and, when the signals represent a rhythm above a programmable value, said therapy device control unit is further configure to only trigger a single anti-tachycardiac stimulation from the right-ventricular and the left-ventricular anti-tachycardia stimulation and, trigger, simultaneously therewith or immediately thereafter, a procedure to charge a shock capacitor for a defibrillation shock.

7. The implantable biventricular cardiac therapy device (10) according to claim 6, wherein the programmable limit value represents a heart rate at which a tachycardia represents fibrillation.

8. The implantable biventricular cardiac therapy device (10) according to claim 6, wherein the therapy device control unit (54) is further configured to check a success of the triggered single anti-tachycardiac stimulation during the charging of the shock capacitor and, suppress a delivery of the defibrillation shock when the success of the triggered single anti-tachycardiac stimulation is detected.

9. The implantable biventricular cardiac therapy device (10) according to claim 1, wherein the implantable biventricular cardiac therapy device (10) is an implantable biventricular cardioverter/defibrillator (ICD) comprising a metallic housing, wherein the metallic housing comprises the therapy device control unit, the right-ventricular stimulation unit, the left-ventricular stimulation unit and electrical components, wherein the electrical components comprise the one or more shock capacitors; and, a connection housing connected to electrode leads, wherein said electrode leads comprise said at least one right-ventricular sensing electrode, said at least one left-ventricular sensing electrode, said at least one right-ventricular stimulation electrode and said at least one left-ventricular stimulation electrode.

* * * * *